(12) United States Patent
Merk et al.

(10) Patent No.: US 10,492,937 B2
(45) Date of Patent: Dec. 3, 2019

(54) DEPLOYING A BALLOON EXPANDABLE STENT TO INDUCE SPIRAL FLOW

(71) Applicant: Cook Medical Technologies LLC, Bloomington, IN (US)

(72) Inventors: James Merk, Terre Haute, IN (US); Brent Mayle, Spencer, IN (US); Ralf Spindler, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 252 days.

(21) Appl. No.: 15/667,092

(22) Filed: Aug. 2, 2017

(65) Prior Publication Data
US 2018/0104078 A1 Apr. 19, 2018

Related U.S. Application Data

(60) Provisional application No. 62/408,872, filed on Oct. 17, 2016.

(51) Int. Cl.
*A61F 2/958* (2013.01)

(52) U.S. Cl.
CPC ...... *A61F 2/958* (2013.01); *A61F 2002/9583* (2013.01); *A61F 2230/0091* (2013.01)

(58) Field of Classification Search
CPC .. A61F 2/86; A61F 2/954; A61F 2/958; A61F 2002/9583; A61F 2230/0091; A61M 25/10; A61M 25/1002; A61M 25/1038; A61M 2025/1004; A61M 2025/1031; A61M 2025/1084; A61M 2025/1086
See application file for complete search history.

(56) References Cited

U.S. PATENT DOCUMENTS

| | | | |
|---|---|---|---|
| 4,762,130 A | 8/1988 | Fogarty et al. | |
| 6,010,530 A * | 1/2000 | Goicoechea | A61F 2/07 623/1.13 |
| 6,527,739 B1 | 3/2003 | Bigus et al. | |
| 7,766,871 B2 | 8/2010 | Hirszowicz et al. | |
| 8,226,704 B2 | 7/2012 | Caro et al. | |

(Continued)

FOREIGN PATENT DOCUMENTS

| | | |
|---|---|---|
| EP | 2848279 | 3/2015 |
| WO | 2015073114 | 5/2015 |

OTHER PUBLICATIONS

European Patent Office, European Search Report for Application No. 17196887.8, Published Feb. 21, 2018, Munich Germany.

*Primary Examiner* — Robert A Lynch
(74) *Attorney, Agent, or Firm* — Liell & McNeil

(57) ABSTRACT

A balloon expanded stent delivery system includes an inflation constraint, such as a wire, spirally wound about the longitudinal axis in contact with a balloon and attached to an underlying catheter. A balloon expanded stent is mounted about the balloon and the inflation constraint. The delivery system has a predeployment configuration with the balloon deflated and the stent unexpanded. The system has a deployment configuration in which the inflation constraint constrains the inflated balloon to a spiral shape, the stent is expanded and in contact with the balloon, and the stent has a flow directing surface with a spiral contour that matches the spiral shape of the balloon. In a postdeployment configuration, the stent retains the flow directing surface with the spiral contour.

14 Claims, 3 Drawing Sheets

(56) References Cited

U.S. PATENT DOCUMENTS

2005/0021070 A1\* 1/2005 Feld .............. A61B 17/320725
                                              606/194
2014/0135891 A1    5/2014 Poehlmann et al.
2016/0022966 A1\* 1/2016 Chuter .............. A61M 25/1002
                                              606/194

\* cited by examiner

DEPLOYING A BALLOON EXPANDABLE STENT TO INDUCE SPIRAL FLOW

TECHNICAL FIELD

The present disclosure relates generally to delivery systems for balloon expanded stents, and more particularly to constraining the balloon to assume a spiral shape to imprint a spiral contour onto the stent during deployment of the stent.

BACKGROUND

A current topic receiving increased attention and research is the modification of hemodynamics to improve stent outcomes. It has been theorized that inducing spiral flow can increase the sheer stress at the surface of an implant, and thereby reduced thrombosis in the implant and reduce restenosis. For instance, U.S. Pat. No. 8,226,704 teaches attachment of an inelastic helical plastic strip to the outer surface of a balloon in order to cause the balloon to assume a helical shape upon inflation. This reference further suggests that, upon inflation, the balloon can cause a stent to adopt the helical geometry of the balloon to create a helical flow lumen when the balloon is deflated and removed after deployment. This reference also teaches modifying a stent to include a helical constraint to supposedly produce the same effect. While the concept may appear sound, modifying either balloon catheters and/or stents with attached helical plastic strips can prove extremely problematic when attempting to transform from an experimental proof of concept to mass production with consistent results.

The present disclosure is directed toward one or more of the problems set forth above.

SUMMARY OF THE DISCLOSURE

In one aspect, a balloon expanded stent delivery system includes a balloon mounted about a catheter that has a longitudinal axis. An inflation constraint is spirally wound about the longitudinal axis in contact with the balloon and attached to the catheter. A balloon expanded stent is mounted about the balloon and the inflation constraint. The delivery system has a predeployment configuration characterized by the balloon being deflated, and the stent is unexpanded and in contact with the balloon. The delivery system has a deployment configuration characterized by the balloon being inflated, the inflation constraint constrains the inflated balloon to a spiral shape, the stent is expanded and in contact with the balloon, and the stent has as flow directing surface with a spiral contour that matches the spiral shape of the balloon. The delivery system has a postdeployment configuration characterized by the balloon being deflated and out of contact with the stent, and the stent retains the flow directing surface with the spiral contour.

In another aspect, a balloon expanded stent delivery system includes a balloon catheter with a catheter and a balloon mounted thereon. The balloon catheter includes a wire attached to the catheter and spirally wrapped on the balloon. A stent is mounted on the balloon. When the balloon is inflated, the stent has a spiral contour that is defined by and responsive to a spiral shape of the inflated balloon as constrained by the wire.

In still another aspect, a balloon catheter for imprinting a stent with a spiral contour during deployment includes a catheter with a longitudinal axis, and a balloon concentrically mounted on the catheter. The balloon has a cylindrical shape when inflated and unconstrained. An inflation constraint is an unattached to, but in contact with, the balloon. The inflation constraint is attached to the catheter and spirally wound about the longitudinal axis in contact with the balloon. The balloon catheter has an inflated configuration characterized by the balloon being inflated, and the inflation constraint constrains the inflated balloon to a spiral shape that includes a spiral valley flanked by a pair of spiral peaks.

DETAILED DESCRIPTION

The present disclosure is directed to a strategy of imprinting a spiral contour on a plastically expanded stent at the time of deployment by expanding the stent with a balloon catheter that assumes a spiral shape when inflated. By imprinting a spiral contour on the inner surface of the stent during deployment, one could expect the stent to desirably induce spiral flow in blood flow through the stent. While the present disclosure contemplates stents that have been modified in some way to better accept an imprinted spiral shape, such as by some spiral arrangement of struts that make up the underlying framework of the stent, the present disclosure may most advantageously apply to conventionally available stents with no special modifying features. For instance, stents that are designed to assume a uniform cylindrical shape upon expansion may be particularly well suited, especially if the underlying framework has sufficient density to permit asymmetric expansion.

Stents according to the present disclosure may include a fabric attached to and/or covering some or all of the stent, and may include stents with a vane(s) or other surface feature that may be deployed to induce spiral flow. Balloon catheters according to the present disclosure may preferably involve typical commercially available balloon catheters that, when unmodified, expand to a regular cylinder shape that is concentric with the underlying catheter. Balloon catheters according to the present disclosure contemplate modifying such a conventional balloon catheter to include a wire that is spirally wrapped in contact with, but unattached to, the underlying balloon so that when the balloon is expanded, the wire constrains the balloon to assume a spiral shape, which in turn imprints a spiral contour on the stent during deployment. The wire may be attached to the underlying catheter rather than the balloon, and this strategy provides engineers with the opportunity to utilize the same underlying balloon catheter but modified with wires having a variety of pitch angles with respect to the longitudinal axis of the underlying catheter, with variations in the number of turns that the wire encircles the balloon, variations in spiral depth, and even double or triple helix designs utilizing two or more wires wrapped in parallel about the balloon to arrive at different spiral shapes that produce desirable outcomes in different circumstances. Thus, the present disclosure contemplates a simple modification to conventional balloon catheters, preferably using unmodified and available stents to provide a solution that is straight forward, adaptable and a low cost method of inducing spiral flow in passageways. The present disclosure teaches a huge number of possible combinations of pitch and depth of spiral deformation which can be imparted on the stent once deployed.

Figure 1:
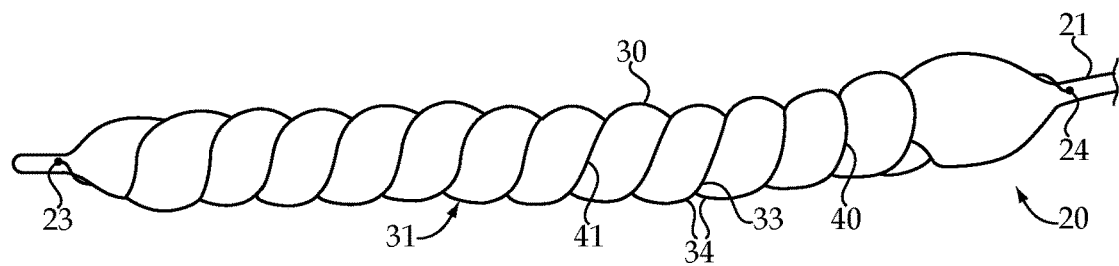
FIG. 1 is a partial side schematic view of a balloon catheter according to the present disclosure.

Referring now to FIG. 1, an example balloon catheter 20 according to the present disclosure includes a balloon 30 mounted about a catheter 21. An inflation constraint 40 is attached to catheter 21 and wrapped onto the balloon 30 to create a spiral shape 31 when the balloon 30 is inflated as shown. In this example, the inflation constraint 40, which may be a wire 41, encircles balloon 30 in excess of ten times. Nevertheless, those skilled in the art will appreciate that the wire 41 need not encircle the balloon even once to still fall within the intended scope of the present disclosure. The spiral shape 31 includes a spiral valley 33 flanked by a pair of spiral peaks 34. In this embodiment, the wire is attached to catheter 21 at a first attachment 23 near the distal end of catheter 21, and attached at a second attachment 24 proximal to balloon 30. Those skilled in the art will appreciate that in the context of the present disclosure the terms proximal and distal refer to locations nearer and farther away, respectively, from a handle (not shown) of the device that is manipulated by an operator, such as a clinician. Although not evident in FIG. 1, balloon 30 may be a conventional balloon in that it would assume a regular cylindrical shape concentric with catheter 21 if inflation constraint 40 were not present. In the context of the present disclosure, the inflation constraint 40 may be metallic, such as a wire 41, or maybe non-metallic and take the form of a composite, a plastic, or maybe even a suture without departing from the present disclosure. The present disclosure also contemplates inflation constraints 40 that do not exhibit any substantial elasticity at the inflation pressures of balloon 30, but inflation constraints 40 that did stretch under the force of the pressurized fluid in balloon 30 would also fall within the scope of the present disclosure.

Thus, one could engineer the depth relationship between the spiral valley 33, the spiral pikes 34 and the outside diameter of the spiral shape 31, among other things, by appropriate choice of inflation constraint 40. An inflation constraint 40 according to the present disclosure means a slender length of material with a circular or oval cross section that is something other than a strip or band of material.

Figure 2:
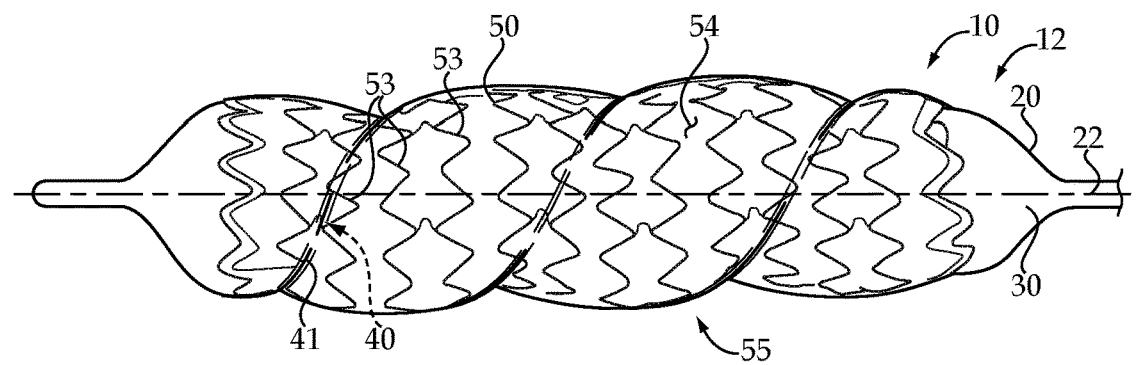
FIG. 2 is a partial side view of a balloon expanded stent delivery system in a deployment configuration according to the present disclosure.
Figure 3:
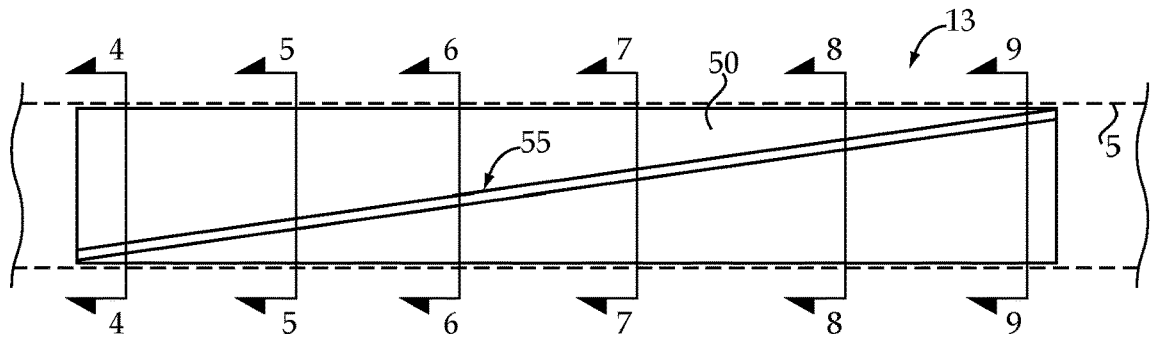
FIG. 3 is a side schematic view of a stent in a postdeployment configuration according to the present disclosure.
Figures 4, 5, 6, 7, 8, 9:
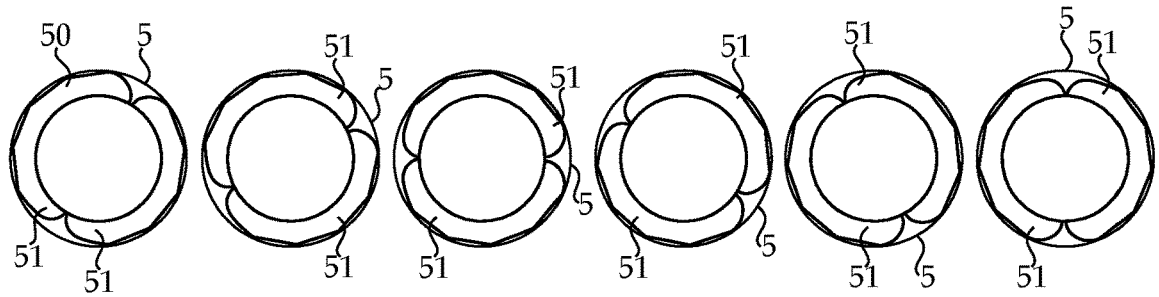
FIG. 4 is a sectioned view through the stent of FIG. 3 as viewed along section lines 4-4.
FIG. 5 is a sectioned view through the stent of FIG. 3 as viewed along section lines 5-5.
FIG. 6 is a sectioned view through the stent of FIG. 3 as viewed through section lines 6-6.
FIG. 7 is a sectioned view through the stent of FIG. 3 as viewed along section lines 7-7.
FIG. 8 is a sectioned view through the stent of FIG. 3 as viewed along section lines 8-8.
FIG. 9 is a sectioned view through the stent of FIG. 3 as viewed along section lines 9-9.

Referring now to FIG. 2, a balloon expanded stent delivery system 10 includes a balloon catheter 20, comprised of a balloon 30 mounted about a catheter 21, which has a longitudinal axis 22. Although different embodiments are shown and described, the same numerals are used to identify the same features throughout this disclosure. An inflation constraint 40 which is illustrated as a wire 41, is spirally wound about the longitudinal axis 22 in contact with the balloon 30 and attached to the underlying catheter 21 of balloon catheter 20. A balloon expanded stent 50 is mounted about balloon 30 and the inflation constraint 40. The delivery system 10 has a predeployment configuration characterized by the balloon 30 being deflated, and the stent 50 being unexpanded and in contact with the balloon 30. The delivery system 10 is shown in a deployment configuration 12 characterized by the balloon 30 being inflated, the inflation constraint 40 constraining the inflated balloon 30 to a spiral shape 31, and the stent 50 is expanded and in contact with the balloon 30. The deployment configuration 12 is also characterized by the stent 50 having a flow directing surface (inner surface of the stent 50) with a spiral contour 55 that matches the spiral shape 31 of the balloon 30. In this example, stent 50 includes a fabric 54 attached to and supported by a framework 53, which is conventional and well known in the art. The term "match" means that the spiral contour 55 is a reverse shape of, and is in phase with, the spiral shape 31 of the balloon 30. The underlying framework 53 of stent 50 could be constructed from any suitable plastically deformable material, including but not limited to deformable alloys such as stainless steel or CoCr and even non-metallic materials known in the art. The fabric 54 could be PTFE, Dacron, silicon, urethane or any other permeable or non-permeable material known in the art. Fabric 54 can be attached to framework 53 in any known way, including but not limited to encapsulating the fabric with two part structures that sandwich the fabric between concentric frameworks, (see e.g. JoStent), encapsulating the stent with two parts of fabric material on the other surfaces, or a solid fabric tube with a disconnected wrap around the framework to bond in the intra-strut spaces (see e.g., Gore Viabhan), or the fabric could be sewn to the framework on the inside and/or the outside, or any other attachment strategy known in the art.

In this example embodiment, the underlying framework 53 and the fabric 54 have a typical symmetric design, but the present disclosure does contemplate stents with asymmetric features that could aide in the introduction of spiral flow after deployment. For instance, the present disclosure contemplates lining up flexible features on a stent in a helical pattern that overlays the constrained balloon to promote enhanced conformability of the stent to the vessel through bending at reduced diameter sections, curves and the like, or even by a portion of a flow directing surface for the spiral contour 55. In any event, the flow would still be altered by the shape of the stent as imprinted by the underlying spiral shape 31 of balloon 30. The delivery system 10 also has a postdeployment configuration characterized by the balloon 30 being deflated and out of contact with the stent 50, while the stent 50 retains the flow directing surface in the spiral contour 55. Although the present disclosure contemplates fabric that does not completely cover the underlying framework 53, the embodiment of FIG. 2 shows the framework 53 covered by a fabric tube, which could be attached to the framework 53 by any of the strategies discussed about.

Referring now to FIGS. 3-9, a stent 50 according to the present disclosure is shown in a postdeployment configuration 13 after the deflation of a spiral shaped balloon 30 to implant stent 50 in a passageway 5, which may be blood vessel of a patient or an artificial passageway for purposes of teaching or testing. In this example, the spiral contour 55 of the stent reveals that the underlying balloon must have had two inflation constraints that each encircled its associated balloon less than once to produce the shape shown. The section views show that a pair of flow directing surfaces 51 spiral through the interior of stent 50 to induce spiral flow on fluid flowing therethrough.

Figure 10:
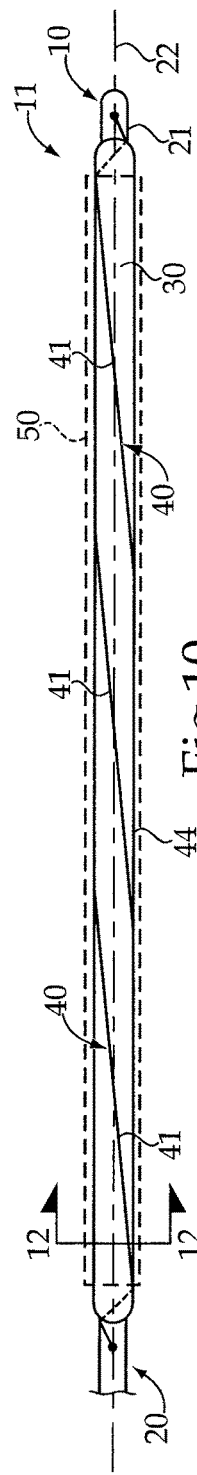
FIG. 10 is a partial side schematic view of a balloon expanded stent delivery system according to the present disclosure in a predeployment configuration.
Figure 11:
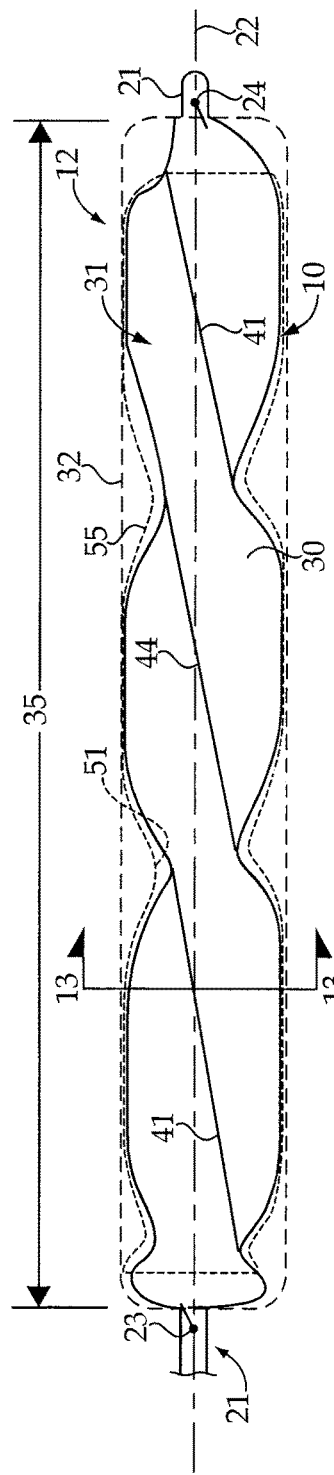
FIG. 11 is a partial side schematic view of a balloon expanded stent delivery system according to the present disclosure in a deployment configuration.
Figure 12:
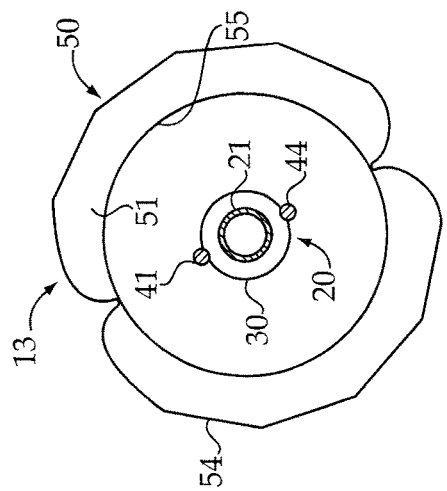
FIG. 12 is a sectioned view through the delivery system of FIG. 10 as viewed along section lines 12-12.
Figure 13:
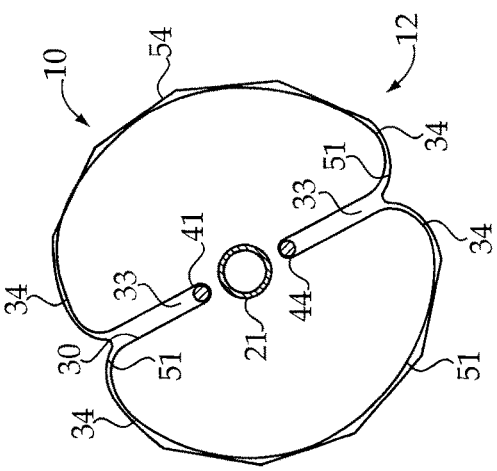
FIG. 13 is a sectioned view through the stent deployment system of FIG. 11 as viewed along section lines 13-13.
Figure 14:
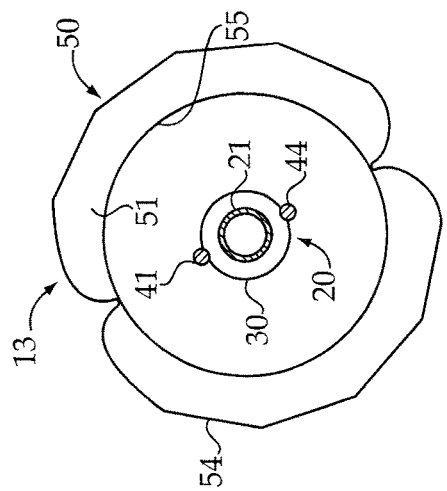
FIG. 14 is a sectioned view through the stent deployment systems of FIGS. 10 and 11 in a postdeployment configuration.

Referring now to FIGS. 10-14, a balloon expanded stent delivery system 10 includes a balloon catheter 20 with a balloon 30 mounted thereon. If unconstrained, balloon 30 would inflate to a regular cylindrical shape 32 (FIG. 11). However, system 10 includes first and second inflation constraints 40 and 44 that encircle the underlying balloon 30 more than once but less than twice. Each of the inflation constraints 40, 44 may comprise a wire 41 that is attached to catheter 21 at a first attachment 23 and a second attachment 24. As in the earlier description, the wires 41 are in contact with, but unattached to, the balloon 30. FIG. 10 shows the system in the predeployment configuration 11, and FIG. 11 shows system 10 in the deployment configuration 12. The spiral shape 31 of the balloon 30 imprints a matching spiral contour 55 on the stent 50 to create a flow directing surface 51 that will induce spiral flow. In this example, the two inflation constraints 40 and 44 are out of contact with each other over a length 35 of balloon 30 so as to define a double helix. FIG. 13 shows a section view as to how the spiral shape 31 defined by the spiral valley 33 and the spiral peaks 34 tend to imprint a spiral contour 55 on the inner surface of stent 50 during the inflation process during deployment. When the balloon 30 is deflated, the system 10 may be placed in a postdeployment configuration 13 as shown in FIG. 14 in which the balloon 30 is out of contact with stent 50, but the stent 50 retains the flow directing surface 51 with the spiral contour 55.

INDUSTRIAL APPLICABILITY

The present disclosure finds general applicability in any balloon expanded stent application. The present disclosure finds specific applicability in balloon expanded stent applications in which there is a desire to impart spiral flow to fluid flowing through the stent after deployment thereof. The present disclosure finds specific applicability in arteriovascular stenting applications in which the inducement of the spiral flow could be expected to improve the outcome by possibly reducing or delaying restenosis of a stented passageway.

Figure 15:
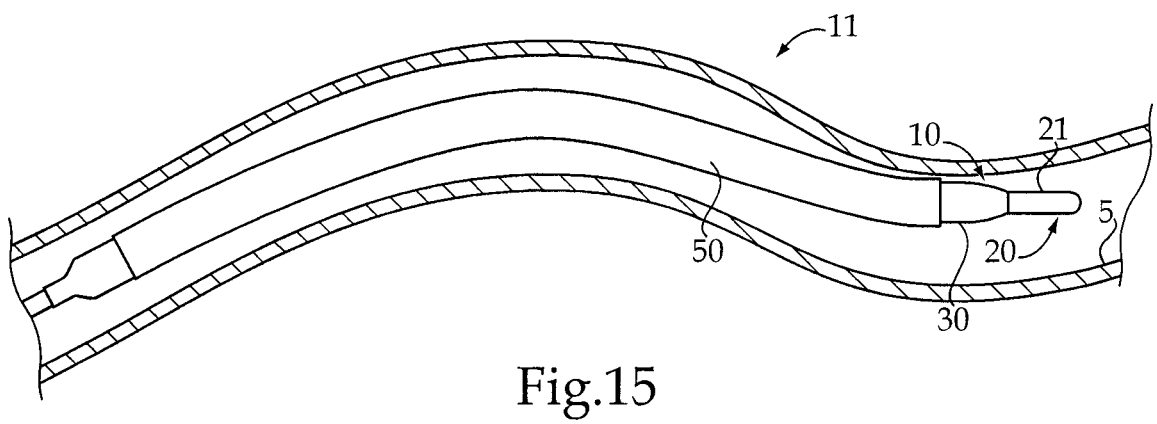
FIG. 15 is a schematic side view of a portion of a stent delivery system in a predeployment configuration within a passageway.
Figure 16:
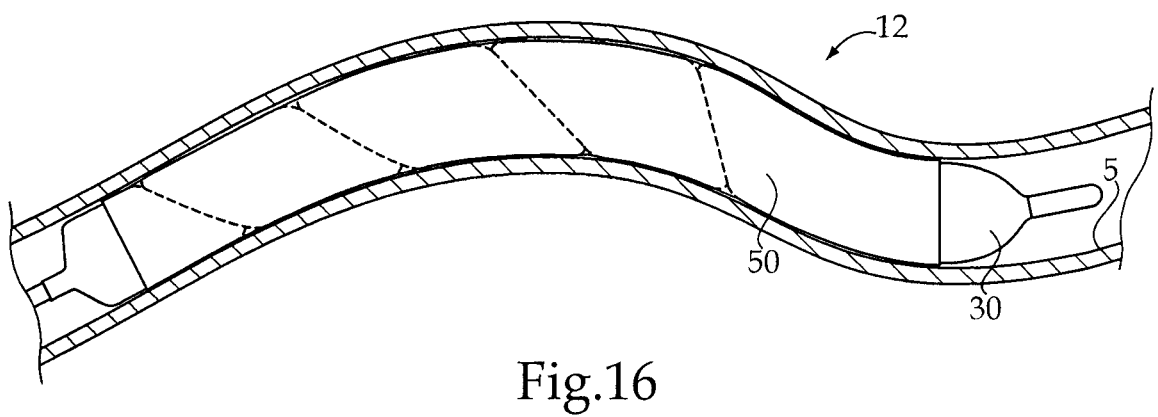
FIG. 16 shows the stent delivery system of FIG. 15 in its deployment configuration.
Figure 17:
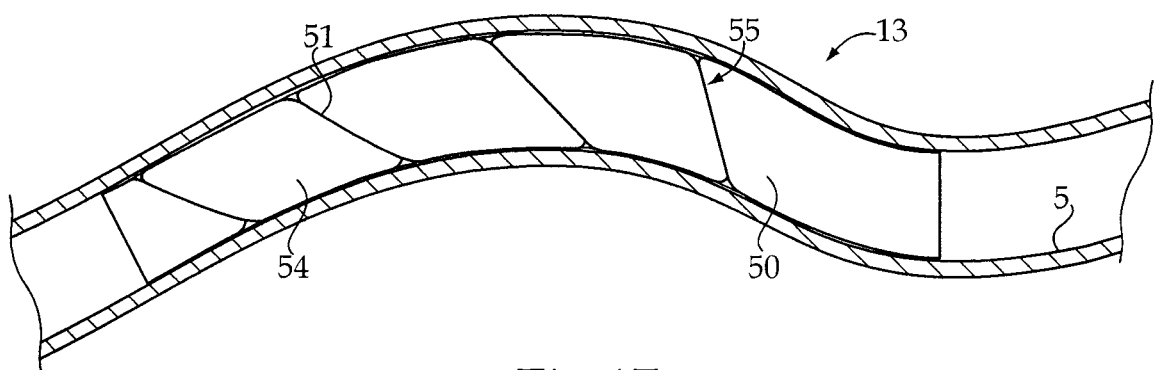
FIG. 17 shows the stent from FIGS. 15 and 16 in a postdeployment configuration.

Referring now to FIGS. 15-17, an example procedure for deploying a stent 50 according to the present disclosure is very similar to known techniques. First, the balloon expanded delivery system 10 is maneuvered through a passageway 5 in a pre-deployment configuration 11. As discussed earlier, the balloon expanded stent delivery system 10 includes a balloon catheter 20 that includes a balloon 30, about which is mounted a yet to be expanded stent 50. FIG. 11 shows stent delivery system 10 in a deployment configuration 12 that is characterized by the balloon 30 being inflated with an inflation constraint 40 constraining the inflated balloon 30 to a spiral shape 31. The stent 50 is expanded and in contact with the balloon 30 and the stent 50 has a flow directing surface 51 with a spiral contour 55 that matches the spiral shape 31 of the balloon 30. FIG. 17 shows the delivery system 10 in a postdeployment configuration 13 in which the balloon 30 has been deflated and moved out of contact with the stent 50, but the stent retains a spiral contour 55 that is defined by, and responsive to, the spiral shape 31 previously defined by the inflated balloon 30, as constrained by the inflation constraint 40. One could now expect fluid flow through passageway 5 and stent 50 to have a spiral motion induced into the flow traveling therethrough.

Those with skill in the art will appreciate that inducing spiral flow can increase sheer stress at the surface of an implant (stent 50) and thereby possibly reduce thrombosis in the implant and reduce the likelihood of restenosis. Unlike some prior art strategies for inducing spiral flow, the present disclosure contemplates the use of unaltered and currently available balloon expanded stents that are normally envisioned as being expanded to assume a regular cylindrical shape, but instead are imprinted with a spiral contour 55 due to the underlying balloon 30 being constrained to a spiral shape 31 by an inflation constraint 40. The balloon catheters 20 of the present disclosure may also rely upon conventionally available balloon catheters that are altered only by the addition of the inflation constraint 40 that is unattached to, but in contact with, the balloon 30. The inflation constraint 40 may be a wire 41 that is attached to the underlying catheter 21 in any suitable manner known in the art.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A balloon expanded stent delivery system comprising:
   a catheter with a longitudinal axis;
   a balloon mounted about the catheter;
   an inflation constraint spirally wound about the longitudinal axis in contact with the balloon and being attached to the catheter;
   a balloon expanded stent mounted about the balloon and the inflation constraint;
   the delivery system having a predeployment configuration characterized by the balloon being deflated, and the stent is unexpanded and in contact with the balloon;
   the delivery system having a deployment configuration characterized by the balloon being inflated, the inflation constraint constrains the inflated balloon to a spiral shape, the stent is expanded and in contact with the balloon, and the stent has a flow directing surface with a spiral contour that matches the spiral shape of the balloon; and
   the delivery system having a postdeployment configuration characterized by the balloon being deflated and out of contact with the stent, and the stent retains the flow directing surface with the spiral contour.

2. The delivery system of claim 1 wherein the inflation constraint includes a wire spirally wound about the balloon and constraining the balloon to the spiral shape when the balloon is inflated.

3. The delivery system of claim 1 wherein the stent includes a fabric attached to and supported by a framework.

4. The delivery system of claim 3 wherein the fabric includes a fabric tube.

5. The delivery system of claim 1 wherein the balloon has a regular cylindrical shape when inflated and unconstrained.

6. The delivery system of claim 1 wherein the spiral shape of the balloon includes a spiral valley flanked by a pair of spiral peaks;
   the inflation constraint is positioned in the spiral valley; and
   a portion of the flow directing surface is positioned between the pair of spiral peaks in the deployment configuration.

7. The delivery system of claim 1 wherein the inflation constraint is one of a plurality of inflation constraints.

8. The delivery system of claim 7 wherein the each of the plurality of inflation constraints are out of contact with each other over a length of the balloon.

9. The delivery system of claim 1 wherein the inflation constraint encircles the balloon at least once.

10. The delivery system of claim 1 wherein the inflation constraint is in contact with, but unattached to, the balloon.

11. A balloon expanded stent delivery system comprising:
    a balloon catheter that includes a catheter with a balloon mounted thereon, and including a wire attached to the catheter and spirally wrapped on the balloon;
    a stent mounted on the balloon; and
    wherein the balloon is inflated and the stent has a spiral contour that is defined by and responsive to a spiral shape of the inflated balloon as constrained by the wire.

12. The delivery system of claim 11 wherein the stent includes a fabric tube attached to and supported by a framework.

13. The delivery system of claim 12 wherein the inflation constraint is in contact with, but unattached to, the balloon.

14. The delivery system of claim 13 wherein the inflation constraint encircles the balloon at least once.

* * * * *